United States Patent [19]

Reid et al.

[11] 4,352,887

[45] Oct. 5, 1982

[54] METHOD AND ARTICLE FOR CULTURING DIFFERENTIATED CELLS

[75] Inventors: Lola C. M. Reid, Rye, N.Y.; Marcos Rojkind, Ciudad Satelite, Mexico

[73] Assignee: Albert Einstein College of Medicine of Yeshiva University, Bronx, N.Y.

[21] Appl. No.: 89,167

[22] Filed: Oct. 29, 1979

[51] Int. Cl.$^3$ .................. C12M 3/00; C12N 5/00; C12N 5/02
[52] U.S. Cl. .................. 435/240; 435/241; 435/284; 435/285; 435/286
[58] Field of Search .............. 435/240, 241, 284, 285, 435/297, 299, 273, 1, 286

[56] References Cited

U.S. PATENT DOCUMENTS 3,034,852  5/1962  Nishihara .................. 435/273 X
4,024,020  5/1977  Weiss et al. .................. 435/241
4,201,845  5/1980  Feder et al. .................. 435/285

OTHER PUBLICATIONS

Meezan et al., *Life Sciences*, vol. 17, (11) Pergamon Press, 1721–1732.
Price, *Chemical Abstracts*, 84:71179k, 194 (1976).
Cleator, *Chemical Abstracts*, 77:123496p, 149 (1972).
Sode et al., *Chemical Abstracts*, 89:152702f, 365–366, (1978).
Reid et al., *Methods in Enzymology, Cell Culture*, vol. LVIII, Academic Press, New York, 263–278, (1979).
Hauschka, *Growth, Nutrition and Metabolism of Cells in Culture*, Academic Press, New York, 90–104, (1972). vol. II.

*Primary Examiner*—Esther M. Kepplinger
*Attorney, Agent, or Firm*—Stephen E. Feldman; Marvin Feldman; Steve T. Zelson

[57] ABSTRACT

A method, solid-state culture support and culture solution are disclosed which enables successful in vitro culturing of differentiated cells, with significant retention of their differentiated character. Through the use of extra-cellular matrix fibers, specifically derived from connective tissue, as culture substrates, the method also discloses the isolation of the connective tissue fibers and their preparation as a culture substrate. This method provides significantly higher survival and attachment rates, and often significantly improved growth properties for in vitro cultures of differentiated cells, especially epithelial, over the current methods for culturing these cells.

This method also significantly enables certain differentiated cells to retain much of their normal enzymatic activities.

Furthermore, this method enables certain differentiated cells to retain to a high degree, their ability to secrete substances, such as hormones.

32 Claims, No Drawings

METHOD AND ARTICLE FOR CULTURING DIFFERENTIATED CELLS

The Government has rights in this invention pursuant to grant Nos. CA 1330-6, AM 17702 and GM 19100.

FIELD OF USE OF THE INVENTION

This invention relates to a method, article and solution for culturing of body cells that are normally in contact with basal lamina material, especially differentiated epithelial cells. Specifically, this invention relates to an *in vitro* method for Zulturing differentiated cells. In a more specific sense, this method relates to a method of preparing the culture substrate for *in vitro* culturing of differentiated cells.

BACKGROUND AND DISCUSSION OF PRIOR ART

It is known that successful *in vitro* culturing of differentiated cells remains especially difficult and elusive when utilizing current cell culture techniques. The lack of established and stable, normal and malignant cultures of differentiated cells has severely hampered certain fields of research, especially cancer studies and treatment.

Currently, the culturing of cells is done primarily with one of three methods:

Organ culture: maintenance of organs separated from their central vascular supply but with the organ, as an entity, left intact.

Tissue culture: culture of tissues or fragmented organs. The "sociocellular" relationships of the tissue architecture are preserved.

Cell culture: culture of an individual cell type divorced from other cell types.

A marked difference in response of explanted cells occurs when they are cultured by cell rather than organ or tissue culture techniques. Methods which retain tissue architecture permit retention of tissue-specific functions including hormonal and pharmacological responses. However, the tissue normally degenerates within a few weeks, due primarily to difficulties in nutrient and waste products exchange. Cell culture procedures overcome this limitation since they use explanted tissues which are disaggregated into single cells. The cells are adpated to grow as a monolayer on a solid-state support such as, treated plastic, or as a cell suspension, and can be maintained in culture for extended periods. Nutrients are supplied by a liquid medium of defined basal composition supplemented with one of various sera. Ideally, one isolates a clonal cell line i.e., a single cell whose progeny are maintained in continuous cell culture. There is genetic uniformity, easier maintenance of the cells, and reduction of variables associated with a multicell culture system. Nevertheless, cell culture procedure usually result in distortion of cellular phenotype and karyotype; normal cells rarely adapt as permanent cell lines without developing abnormal karyotypes or losing tissue-specific functions; malignant cells adapt more easily than do benign tumor cells or normal cells; and fibroblasts or stromal components become established preferentially over epithelial cells. The difficulties of establishing differentiated cells in cell culture have been attributed to many causes. These include an inadequately defined basal medium; inadequately defined hormone requirements; the static conditions of cell culture in which nutritional and oxygen gradients develop and limit the growth and functioning of cells with strict nutritional and oxygen requirements; and loss of or damage of cell-cell junctions, perhaps essential in growth and/or differentiation or both by the cell culture procedures of mechanical and enzymic dissociation into single cell suspensions. Undoubtely all of these have contributed to the impasse in maintaining differentiated cells in cell culture. Yet despite progress on these various fronts, the goal of routinely culturing normal differentiated cells remains elusive.

In a published article, namely, vol. LVIII of the *Methods in Enzymology*, entitled "New Techniques for Culturing Differentiated Cells: Reconstituted Basement Membrane Rafts" by L. M. Reid and M. Rojkind, cell culture techniques were set forth which were, in essence, attempts to simulate some of the cell-cell relationships and of the tissue matrix relevant to epithelial cells. The techniques described involved the culturing of epithelial cells on substrates of reconstituted basement membrane and in medium supplemented with hormones, serum, and with conditioned medium from feeder layers. That technique, more specifically, involved utilization of reconstituted basement membrane rafts on which were floated epithelial cells over primary cultures of mesenchymal cells normally in association with the epithelial cells. This is, therefore, not applicable to the disclosed technique which involves connective tissue-derived fibers as a substrate for body cells that are normally in contact with basal lamina material, especially differentiated epithelial cells, in cell cultures. Basal lamina material as used herein is a substance found on the surface of differentiated cells, on the basal side or surrounding said cells, and is composed of collagens, carbohydrates including glycosaminoglycans and non-collagenous proteins.

In a published article, namely, Vol. 2d. 17 of the *Life Sciences*, entitled "A Simple, Versatile, Nondisruptive Method for the Isolation of Morphologically and Chemically Pure Basement Membranes from Several Tissues" by Elias Meezan, J. Thomas Hjelle and Klause Brendel, a procedure was set forth for the isolation of intact basement membranes from bovine retinal and brain blood vessels, rabbit renal tubules and rat renal glomeruli. The techniques described involved a seven step procedure, with several steps utilizing primarily high concentrations of a Sodium Deoxycholate solution, concentrations much higher than in the disclosed technique. Other solutions used in the Meezan procedure contained sodium azide, sodium chloride and DNase. This procedure differs significantly from the disclosed technique is that using the Meezan procedure the resultant isolated membranes are partially denatured and not in a form usable by cells in culture. The disclosed technique, however, requires the use of functionally active, non-denatured, connective tissue-derived fibers and these, may only be acquired using the disclosed technique with its different steps, compounds and concentrations. Another significant distinction is that the disclosed method involves the use of ribonuclease in addition to DNase. The use of ribonuclease and DNase enables the production of truely pure connective tissue derived fibers, without any contaminating DNA or RNA, and this is essential for use as a culture substrate. The Meezan procedure does not use Ribonuclease. The use of DNase in the Meezan article to prevent "viscous gel" like DNA from interfering with the isolation procedure would not result in a pure enough or functional product required when using connective tissue-derived fibers as a culture substrate.

It is therefore an object of this invention to provide a method for the establishment of *in vitro* cultures of human or animal differentiated cells.

It is another object of this invention to provide a method as aforesaid in which human or animal differentiated cells are cultured using an extracellular matrix, more specifically, connective tissue-derived fibers, as a substrate.

It is a further object of this invention to provide a method which is applicable to both normal and malignant cells whatever their degree of differentiation.

It is still a further object of this invention to provide a method which significantly improves the survival and attachment rates for *in vitro* cultures of differentiated cells.

It is still another object of this invention to provide a method which significantly improves the growth properties of *in vitro* cultures of differentiated cells which are capable of growth *in vitro*.

It is still a further object of this invention to provide a method which will permit differentiated cells to retain a significant degree of their differentiated state.

It is still another object of this invention to provide a method which permits certain differentiated cells to retain much of their normal enzymatic activities.

It is still a further object of this invention to provide a method which permits certain differentiated cells to retain to a high degree, their ability to secrete substances such as hormones.

It is also an object of this invention to provide a method for the preparation and isolation of a novel culture substrate.

It is another object of this invention to provide tissue-specific connective tissue-derived fibers for the culturing of the related tissue-specific differentiated cells, both normal and malignant.

It is still a further object of this invention to provide a cell culture environment comprising a plurality of fibers as support for the cells with or without other solid state support(s) such as a petri dish or test tube, wherein differentiated cells would have an environment more nearly approximating normal tissue conditions.

The aforesaid objects as well as the other objects and advantages will be made more apparent in reading the following description and the adjoined claims.

DESCRIPTION OF THE PREFERRED EMBODIMENTS

Broadly stated, the method and the culture dish of the present invention are for *in vitro* culturing of differentiated cells comprising the *in vitro* cell culture utilization of substrates whereby differentiated cell cultures retain a significant degree of their differentiated state.

Stated in more specific terms, the present invention comprises a method and culture plate for *in vitro* culturing of mammalian differentiated cells, whether normal or malignant. This comprises providing connective tissue-derived fibers as a cell culture substrate which is either suspended in a solution or attached to a culture plate or other solid state support whereby differentiated cells present on said solid state support or in solution may grow in number over time while substantially retaining their differentiated state.

By the term "connective tissue-derived fibers" as used hereinbefore and hereinafter through the specification and claims, it is meant a substance derived from connective tissues of human or animals which is composed from materials selected from the group consisting of collagens, non-collagenous proteins, and carbohydrates.

In a more specific aspect of this invention, the method comprises:

A. isolation of connective tissue fibers from organ tissue;

B. placing connective tissue fibers onto solid-state supports and spreading them over the solid-state support, or placing the connective tissue fibers into solution and mixing them in suspension;

C. sterilizing the solid-state support or solution after adding the connective tissue fibers;

D. adding the differentiated cells desired to be cultured to the solid-state support or solution and E. providing an operating temperature optimal for those cells.

The immediately aforesaid method enables the differentiated epithelial cells to retain a significant degree of their differentiated state in the culture for as long as one month or longer, so long as nutrients adequate to insure the survival of the cultured cells over this longer period are supplied.

In a preferred aspect of this invention, the method comprises:

A. isolation of connective tissue fiber from liver tissue;

B. placing connective tissue-derived fibers onto the solid-state support and spreading the fibrous matrix to cover said solid-state support wherein the cells are to be cultured.

C. sterilizing the solid-state support after adding the connective tissue-derived fibers;

D. adding differentiated cells desired to be cultured to the solid-state support; and E. providing an operating temperature optimal for these cells and between 0° and 100° C.

It is to be borne in mind that pursuant to the present invention the human or animal differentiated cells may be cultured on a matrix derived from the same organ as the cells to be cultured, but not necessarily derived from the same species.

Another aspect of the present invention relates to a method for preparation and isolation of connective tissue-derived fibers comprising:

1. Homogenizing, blending or dispersing tissue by mechanical or non-mechanical means;

2. Filtering suspension from step 1 and adding filtrate to a detergent solution;

3. Filtering solution from step 2 and adding filtrate to a salt solution;

4. Filtering solution from step 3 and adding filtrate to a salt solution also containing DNase and Ribonuclease;

5. Filtering solution from step 4 and rinsing filtrate first with a saline solution and then with the medium to be used in the culture;

6. Storing fibers in a salt solution supplemented with cryoprotective agents.

It is also contemplated that the separation of the solution components be by centrifugation. It is further contemplated that the isolated connective tissue fibers may be stored frozen in a salt solution with a cryoprotective agent or may be sterilized and then stored at temperatures above freezing.

Another aspect of the present invention relates to a method for *in vitro* culturing of differentiated cells comprising:

A. isolating connective tissue derived fibers from organ tissue;

B. providing the fibers as a substrate for an *in vitro* differentiated cell culture.

The immediate aforesaid method has been found to permit the differentiated cells in the *in vitro* culture to remain substantially in their differentiated state. The immediate aforesaid method is operable and could be conducted at a temperature appropriate to the cells of interest.

It is an important aspect of this invention that the time period that the immediate aforesaid method permits differentiated cells to remain in their substantially differentiated state for at least one month or longer, so long as appropriate nutrients, hormones, growth factors and transfer factors (either pure or in the form of sera or plasma) are supplied to insure the survival of the cells in culture. This method also provides an attachment efficiency for the differentiated epithelial cells *in vitro* that is significantly greater than in the absence of the proposed connective tissue-derived matrix.

Another aspect of the present invention relates to a solid-state support, cell culture article composed of any desired material such as glass or plastic and comprising;

A. a solid-state cell culture support comprising a sterile base support alone or in combination with a cover;

B. a plurality of fibers on the base support or cover.

It is also within the scope of the invention to provide a solid-state cell culture support including fibers comprising connective tissue-derived fibers that cover and are attached to the substrate, e.g. base support, which may be prepared in advance and stored under sterile conditions awaiting later inoculation with differentiated cells.

The preferred embodiment of this method comprises providing tissue culture articles of various sorts precoated with the organ-specific connective tissue-derived fiber matrix. The preferred embodiment of this method is operable for cell maintenance at temperatures optimal for the cells, between 0° C. and 100° C.

Another aspect of the present invention relates to a cell culture environment which comprises tissue-specific connective tissue-derived fibers in suspension within a solution. The tissue-specific fibers are from organ tissues and are placed in suspension in a solution further comprising a medium supplemented with cell-specific hormones or with plasma or serum (or with a combination of any of them) and with conditioned medium from cultures of mesenchymal cells or with factors derived from them.

The term conditioned medium as used herein is a medium in which other cells have been previously cultured and which has been subsequently filtered and into which certain cellular by-products of the initial cell culture has been incorporated. The cellular by-products which had been incorporated into said conditioned medium by the initial cell culture, if isolated, are what is meant by use of the term "factors derived from culture of mesenchymal cells." The solution is operable for cell growth at temperatures optimal for their growth 0° and 100° C.

EXAMPLE I

This example demonstrates the applicability of the present method to *in vitro* cultures of differentiated cells (the most difficult to culture with retention of differentiation) where other culture techniques are essentially ineffective.

This investigation involved the use of three laboratory animals:
1. BALC/C nude mice
2. Adult female Syrian Hamsters
3. Sprague—Dawley rats This investigation also involved the introduction of two transplantable tumor lines into either the adult female Syrian hamsters or athymic nude mice:
1. Syrian Hamster Insulinoma (SHI) (epithelioid cells).
2. Human prostatic tumor Line, R 198 (epithelioid cells).
3. Rat normal hepatocytes (epithelioid cells).

The Syrian Hamster Insulinoma forms soft, well-vascularized tumors in hamsters and athymic nude mice. The tumors are functional, containing significant amounts of insulin (25 units insulin/mg protein).

The human prostatic tumor line, R198, was developed as a transplantable tumor in BALB/c nude mice. It is androgen-dependent for growth and morphology, secretes small amounts of tartrate-inhibitable acid phosphatase, has a human LDH isoenzyme profile, and a prostatic adenylate kinase isoenzyme profile. It is routinely maintained in male BALB/c nude mice.

Tumors are dissected sterily from the animals, weighed, minced finely, and pressed through an 18 gauge needle into the barrel of another syringe. They are then injected subcutaneously into the next hosts.

Syrian Hamster Insulinomas were used directly from the hamster or were passaged at least twice through nude mice. Tumors, either R 198 or insulinomas were dissected from the mice and minced finely. The mince was then treated with antimouse antiserum to provide pure epithelial cell suspensions with no mouse cell contaminents for all experiments analyzing the role of the stroma in the survival, differentiation and/or growth of the cells.

The cells were cultured in a 1:1 mixture of Dulbecco's modified Eagle medium (DME) and Ham's F12 supplemented with trace elements, Hepes, and with 10% Fetal Bovine Serum. The medium is referred to as DME/F12+FBS.

The cells were grown on one of three possible substrates: plastic tissue culture dishes, Type I collagen rafts, or connective tissue fibers. Generally, collagen is extracted from tendon fibers dissected from the tail of a rat or the skin of an animal, such as a rat, mouse, or guinea pig. The connective tissue fibers were prepared and isolated from the livers of Sprague-Dawley rats or from various bovine tissues. The connective tissue fibers may be isolated from the organ tissue of any animal.

The collagen class of proteins is a heterogeneous group of proteins that nevertheless is characterized generally by a unique amino acid composition (about 30% glycine, 20% proline, 20% hydroxyproline, and a variable content of hydrooxylysine). To date, three distinct collagens have been isolated from interstitial tissues and characterized on the basis of the uniqueness of their individual polypeptide chains. These are designated as Type I, Type II, and Type III collagens. Type I collagen is the only collageous component of bone, tendon, and tooth. This type of collagen is also present with other collagens in skin, liver, heart and kidney.

Epithelial cell suspensions (Syrian Hamster Insulinoma cells or R198 cells) were added to plates containing sterilized Type I collagen rafts or to the connective tissue-derived fibers and incubated overnight at 37° C. in an incubator flushed with 95% air and 5% $CO_2$. Once the cells were attached to the Type I collagen substrates, the gelatinous layers were released to form rafts by rimming them with a sterile spatula. The rafts can be transferred from one plate to another by gentle pipetting with a large mouth pipette.

The connective tissue substrates were not detached from the bottom of the dishes.

The cultures that survived for 4 to 6 months, namely only those maintained on the special matrix, were photographed using phase microscopy. For histological sections, the cell cultures were fixed with Bouin's or buffered formaldehyde, dehydrated with an ethanol series, embedded in paraffin, and sectioned at $8\mu$. They were then stained with one of the following: haematoxylin/eosin, Periodic Acid Schiff (PAS), Silver Elastin, or Masson's Trichrome.

In order to determine the attachment and survival efficiency of the cultured epithelial cells with or without stromal feeder layers were added to 60 mm dishes with one of the possible substrates. The cultures were provided with a medium of DME/F12+FBS and incubated at 37° C. in an incubator flushed with 95% air and 5% $CO_2$. The cultures were maintained for 3 days and then terminated. The attachment efficiency was determined by removing the medium from the plates, rinsing the plates 3 times with PBS, fixing with buffered formaldehyde, rinsing with a glycine buffer, and staining with Acridine Orange to reveal the cells. The colonies of cells were then counted. In those plates containing feeder layers, the plates were initially treated for 1 hour with antimouse antiserum plus complement prior to staining with acridine orange.

In order to perform growth studies, the SHI cells were seeded onto the appropriate substrates at seeding densities of either $10^5$ or $10^6$. Triplicate cultures were counted every third day for 4 weeks. The cells to be counted were enzymatically digested away from their substrates with 0.1% type I collagenase+0.1% Trypan Blue in serum-free medium. The cells were then counted with a Coulter Counter as well as assayed for viability by the Trypan Blue Exclusion test. Those plates containing mixed cultures of feeder layers and SHI or 198 cells were treated with antimouse antiserum plus complement for 1 hour prior to detachment of the epithelial cells from the plates.

The general composition of the rat liver connective tissue derived fibers is summarized in Table 1.

In addition, as shown by the culture studies and indicated on Tables 2 and 3, the SHI and R198 cells require both collagenous substrates and factors from the stromal components in order to survive long-term and/or grow. The connective tissue derived fibers provided a substrate of superior quality for maintaining both the SHI and R198 cells in culture as compared to the Type I collagen rafts or plastic tissue culture dishes. In contrast to the connective tissue-derived fibers, the rafts contain primarily Type I collagen plus some small amounts of basement membrane collagen, and trace amounts of LETS protein and glycosaminoglycans. The data indicating the superior quality of the connective tissue-derived fibers over the Type I collagen rafts as a substrate suggest that a combination of several of the components may be necessary for maintaining the epithelial cells in culture.

This example clearly suggests that the connective tissue-derived fibers or substrates made from their essential components may dramatically improve the survival and growth capabilities of differentiated cell in vitro.

TABLE 1

COMPOSITION OF ISOLATED RAT LIVER CONNECTIVE TISSUE DERIVED FIBROUS MATRIX

A. CHEMICAL ANALYSIS

| | COLLAGENS (mg/100 mg protein) | TYPES OF COLLAGEN (% of total collagen) | NON-COLLAGENOUS PROTEINS (mg/100 mg protein) | CARBOHYDRATES ($\mu$ moles glucose equiv/100 mg protein) |
|---|---|---|---|---|
| Prep I | 63.7 | Type 1 (29.9%) Type III (42.7%) Type IV (6.2%) A + B Undefined (20.9%) | 36.2 | 9.0 |
| Prep II | 60.9 | As above | 39.1 | 10.0 |

B. PROPORTION OF RAT LIVER RECOVERABLE AS FIBROUS MATRIX $\left(\text{given as } \frac{\text{amount in fibers}}{\text{amount in liver}} \times 100 = \% \pm \text{S.D.}\right.$

| WEIGHT (gms)* | TOTAL PROTEIN (mgs)*** | TOTAL COLLAGEN (mgs)** | NON-COLLAGENOUS PROTEINS (mgs) |
|---|---|---|---|
| $\frac{0.114}{10.0} \times 100 = 1.14\% \pm 0.29\%$ | $\frac{14.1}{1600} \times 100 = 0.87\%$ | $\frac{8.5}{10.0} \times 100 = 82.8\%$ | $\frac{5.6}{1590} \times 100 = 0.35\%$ |

*The yield of fibers by weight is the average of 50 normal rat livers
**The % yield of collagen in the fibers is the average of 5 normal rat livers
***The % yield of total protein and non-collagenous proteins is the average of 2 normal rat livers.

TABLE 2

GROWTH OF SYRIAN HAMSTER INSULINOMA CELLS ON VARIOUS SUBSTRATES

| SUBSTRATE | FEEDER +/−LAYER | SEEDING DENSITY | # INSULINOMA CELLS AFTER 1 MONTH / # INSULINOMA CELLS ATTACHED DAY 1 |
|---|---|---|---|
| Plastic | + | $10^5$ | 4.9% |

TABLE 2-continued

GROWTH OF SYRIAN HAMSTER INSULINOMA CELLS ON VARIOUS SUBSTRATES

| SUBSTRATE | FEEDER +/− LAYER | SEEDING DENSITY | # INSULINOMA CELLS AFTER 1 MONTH / # INSULINOMA CELLS ATTACHED DAY 1 |
|---|---|---|---|
| (tissue culture dish) | + | $10^6$ | 2.7% |
|  | − | $10^5$ | 0 |
|  | − | $10^6$ | 0 |
| Type I Collagen Raft | + | $10^5$ | 295.0% |
|  | − | $10^6$ | 113.0% |
|  | − | $10^5$ | 48.0% |
|  | − | $10^5$ | 52.0% |
| Connective Tissue-derived matrix | + | $10^5$ | 1000.0% or more |
|  | + | $10^6$ | 1000.0% or more |
|  | − | $10^5$ | 100.0% |

TABLE 3

ATTACHMENT AND SURVIVAL EFFICIENCY OF SYRIAN HAMSTER INSULINOMA CELLS ON VARIOUS SUBSTRATES

| SUBSTRATE | +/− FEEDER LAYERS | ATTACHMENT EFFICIENCY |
|---|---|---|
| Plastic (tissue culture dish) | + | 0.8% |
|  | − | 0 |
| Type I Collagen Raft | + | 43.0% |
|  | − | 24.0% |
| Connective Tissue-derived fiber matrix | + | 50–86.0% |
|  | − | 50–86.0% |

What is claimed is:

1. A method for in vitro culturing of differentiated cells comprising providing connective tissue-derived fibers comprising collagens, non-collagenous proteins and carbohydrates as a substrate for an in vitro differentiated cell culture whereby the differentiated cell culture remains substantially differentiated.

2. The method of claim 1, wherein the temperature at which the method is conducted is between 0° C. and 100° C.

3. The method of claim 2, wherein the temperature at which the method is conducted for mammalian cells is between 29° C. and 42° C.

4. The method of claim 2, wherein the temperature at which the method is conducted is optimal for the cellular growth in vitro.

5. The method of claim 1, wherein the differentiated cells in culture remain differentiated for at least about one month on the connective tissue—derived fibrous substrate so long as nutrients for the cells are provided.

6. The method of claim 1, wherein the differentiated cells are mammalian.

7. The method of claim 1, wherein the differentiated cells are non-mammalian cells.

8. The method of claim 1, wherein the differentiated cells are epithelial cells.

9. The method of claim 1, wherein the differentiated cells are body cells that are normally in contact with basal lamina material.

10. The method of claim 1, wherein the differentiated cells are normally-growing cells.

11. The method of claim 1, wherein in the differentiated cells survive in vitro in a differentiated state.

12. The method of claim 1, wherein the differentiated cells are malignantly-growing cells.

13. The method of claim, 1 wherein the connective tissue-derived fibers are isolated from organ tissue.

14. The method of claim, 1 further comprising placing the connective tissue-derived fibers onto culture solid-state supports and allowing said fibers to cover said solid-state supports.

15. The method of claim 14, further comprising sterilizing said solid-state supports after adding the connective tissues-derived fibers.

16. The method of claim 15, further comprising adding the differentiated cells to the tissue culture plates after sterilization.

17. The method of claim 14, wherein the connective tissue-derived fibers attach to the solid-state support.

18. The method of claim 1, wherein certain differentiated cells in culture exhibit a growth rate of at least 300% as measured by the rate of the number of differentiated cells after one month to the number of differentiated cells that attached day 1 of the culture.

19. The method of claim 1, wherein certain differentiated cells in culture exhibit a growth rate of about 1000% as measured by the ratio of the number of differentiated cells after one month to the number of differentiated cells that attached day 1 of the culture.

20. The method of claim 1, wherein the time period the differentiated cells in culture remain essentially differentiated is at least about one month and is proportional to the presence of the fibrous substrate and nutrients for the cells.

21. The method of claim 1, wherein the attachment efficiency of differentiated cells of the in vitro culture is at least 50%.

22. The method of claim 1, wherein the attachment efficiency of the differentiated cells of the in vitro culture is up to and including 86%.

23. A cell culture solid-state support consisting essentially of a base support for containing a culture medium and said cells cultured thereon and a plurality of connective tissue derived fibers disposed within said base support, said connective tissue-derived fibers consisting essentially of collagens, non-collagenous proteins and carbohydrates.

24. The cell culture solid-state support of claim 23, further comprising a basal medium supplemented with hormones and with conditioned medium including factors derived from cultures of mesenchymal cells.

25. The cell culture solid-state support of claim 23, further comprising a basal medium supplemented with plasma and with conditioned medium including factors derived from cultures of mesenchymal cells.

26. The cell culture solid-state support of claim 23, further comprising a basal medium supplemented with serum and with conditioned medium including factors derived from cultures of mesenchymal cells.

27. The cell culture solid-state support of claim 23, further comprising a basal medium supplemented with hormones and plasma and with conditioned medium including factors derived from cultures of mesenchymal cells.

28. The cell culture solid-state support of claim 23, further comprising a basal medium supplemented with hormones and serum and with conditioned medium including factors derived from cultures of mesenchymal cells.

29. The cell culture solid state support of claim 33, wherein said connective tissue-derived fibers are attached to said base support.

30. The cell culture solid-state support of claim 23, wherein said connective tissue-derived fibers cover said base support.

31. The cell culture solid-state support of claim 23, said connective tissue-derived fibers being from organ tissue.

32. The cell culture solid-state support of claim 23, being operable for cell growth between 0° C. and 100° C.

* * * * *